US012569127B2

(12) United States Patent

Jen

(10) Patent No.: US 12,569,127 B2

(45) Date of Patent: Mar. 10, 2026

(54) MULTI-VIEW VIDEO LARYNGOSCOPE, AND SPATULA BLADE CONFIGURED WITH MULTIPLE IMAGE CAPTURING APPARATUSES

(71) Applicant: Li Way Chang, New Taipei City (TW)

(72) Inventor: Chih-Min Jen, New Taipei City (TW)

(73) Assignee: Li-Way Chang, New Taipei City (TW)

( * ) Notice: Subject to any disclaimer, the term of this patent is extended or adjusted under 35 U.S.C. 154(b) by 201 days.

(21) Appl. No.: 18/255,484

(22) PCT Filed: Dec. 3, 2020

(86) PCT No.: PCT/CN2020/133571

§ 371 (c)(1),
(2) Date: Aug. 2, 2023

(87) PCT Pub. No.: WO2022/116080

PCT Pub. Date: Jun. 9, 2022

(65) Prior Publication Data

US 2024/0315547 A1 Sep. 26, 2024

(51) Int. Cl.
*A61B 1/267* (2006.01)
*A61B 1/00* (2006.01)
(Continued)

(52) U.S. Cl.
CPC .......... *A61B 1/267* (2013.01); *A61B 1/00016* (2013.01); *A61B 1/00045* (2013.01);
(Continued)

(58) Field of Classification Search
None
See application file for complete search history.

(56) References Cited

U.S. PATENT DOCUMENTS 5,800,344 A * 9/1998 Wood, Sr. .............. A61B 1/267
600/196
2016/0250432 A1 9/2016 Hendrix
(Continued)

FOREIGN PATENT DOCUMENTS

CN 102481429 A 5/2012
CN 202386670 U 8/2012
(Continued)

*Primary Examiner* — Tessa M Matthews
(74) *Attorney, Agent, or Firm* — MUNCY, GEISSLER, OLDS & LOWE, P.C.

(57) ABSTRACT

A multi-view video laryngoscope (1), comprising a handle (11), a spatula blade (12), a first image capturing apparatus (13) and a second image capturing apparatus (14). The spatula blade (12) is detachably connected to the handle (11). The spatula blade (12) comprises a junction (121), a side plate (122) and a transverse plate (123). The junction (121) is detachably connected to one end of the handle (11). The side plate (122) extends outwards from the junction (121). The transverse plate (123) bends and extends outwards from one side of the side plate (122). The first image capturing apparatus (13) is arranged on the side of the side plate (122) that is away from the transverse plate (123), and captures a first image (P1). The second image capturing apparatus (14) is arranged on the transverse plate (123) and is located on or adjacent to the central axis of the transverse plate (123), is farther away from the junction (121) than the first image capturing apparatus (13), and captures a second image (P2).

15 Claims, 6 Drawing Sheets

(51) Int. Cl.

| | | |
|---|---|---|
| *A61B 1/05* | (2006.01) | |
| *A61B 1/06* | (2006.01) | |
| *A61B 1/32* | (2006.01) | |

(52) U.S. Cl.
CPC .............. *A61B 1/05* (2013.01); *A61B 1/0676* (2013.01); *A61B 1/32* (2013.01)

(56) References Cited

U.S. PATENT DOCUMENTS

| | | | |
|---|---|---|---|
| 2019/0261844 A1 | 8/2019 | Walker et al. | |
| 2020/0015832 A1* | 1/2020 | Levine | ................... A61B 17/02 |
| 2020/0178780 A1* | 6/2020 | Dan | .................... A61B 1/0005 |

FOREIGN PATENT DOCUMENTS

| | | |
|---|---|---|
| CN | 203447261 U | 2/2014 |
| CN | 204542038 U | 8/2015 |
| CN | 208769744 U | 4/2019 |
| TW | M243171 U | 9/2004 |
| TW | M427913 U | 5/2012 |
| TW | M526871 U | 8/2016 |

* cited by examiner

MULTI-VIEW VIDEO LARYNGOSCOPE, AND SPATULA BLADE CONFIGURED WITH MULTIPLE IMAGE CAPTURING APPARATUSES

BACKGROUND

Technology Field

The disclosure relates to a laryngoscope and, in particular, to a multi-view video laryngoscope.

Description of Related Art

Regarding the conventional laryngoscope as described in Taiwan Patent No. M243171, it disclosed a laryngoscope device 1 used as an auxiliary guiding tool during artificial tracheal intubation. Wherein, the laryngoscope device 1 is composed of a lighting device 10 and a blade 20. The blade 20 has a crescent-shape, and includes a spatula (tongue depressor) part 21, which can be inserted into the patient's mouth and press against the patient's tongue to lift the position of the epiglottis cartilage. The tail end of the spatula part 21 is configured with a light source rod 28, and the light emitted by the lighting device 10 can be led out through the light source rod 28 to produce a light irradiation effect, thereby facilitating the intubation procedure.

The operator usually performs tracheal intubation with the above-mentioned conventional laryngoscope by a directly observation through the patient's lips, mouth and throat so as to find out the tracheal entrance (glottis). This method is called direct laryngoscopy. If the structure in the patient's deep larynx cannot be clearly observed, the endotracheal tube cannot be inserted into the patient's trachea within a critically short period of time, which may cause hypoxia that can endanger the patient's life. The so-called difficult airway refers to the situations of some patients that the operator cannot clearly observe the trachea entrance (glottis), so that the endotracheal tube cannot be inserted into the trachea correctly or may be inserted into the adjacent esophagus by mistake. If these mistakes cannot be solved in time, it will soon lead to hypoxia and even death of the patient. This occurs in patients with stubby neck, swollen tongue, oropharyngeal infection history, surgery, deformation, congenital structural abnormality, or surgery or radiation therapy history to the neck. When difficult airway occurs, the patient's condition will deteriorate rapidly in a short period of time. If the patient cannot be well treated in time, it will quickly lead to hypoxia and death of the patient. Therefore, the medical community needs to improve and develop better endotracheal intubation equipment to overcome this extreme danger status. In view of this, relevant industries and companies have successively developed various video laryngoscopes with image capturing and image displaying functions as a response.

Subsequently, a laryngoscope with image capture/display function was developed, as described in Taiwan Patent No. M427913, which discloses that a video laryngoscope assembly 05 includes a lens handle 10, an image display panel 20 and an arc-shaped combined lens blade 60. In this case, the image display panel 20 is connected with the first end 11 of the lens handle 10, the combined lens blade 60 is connected with the second end 12 of the lens handle 10, and the front end of the combined lens blade 60 is configured with an image capturing device 92 and a lighting member 93. During the endotracheal intubation, the image display panel 20 can display the image captured by the image capturing device 92 in real time, so that the medical personnel can adjust the angle and position of the combined lens blade 60 pressing against the patient's tongue in real time, thereby making the endotracheal intubation work smoothly.

However, the above-mentioned conventional video laryngoscope assembly 05 still has the following disadvantages:

First disadvantage: The combined lens blade 60 only includes one single image capturing device 92, so that the viewing angle thereof is not wide enough. Because the internal structures of different patient's mouths are not the same, when the combined lens blade 60 is inserted into the mouth and presses against the patient's tongue, in some cases, the image capturing device 92 may not quickly and effectively capture the position of the trachea at the patient's larynx.

Second disadvantage: It is even necessary to temporarily replace the combined lens blade 60 with a different radian, so that the image capturing device 92 can capture the position of the trachea at the patient's larynx. As a result, not only the endotracheal intubation operation is delayed, but also the second insertion of the combined lens blade 60 can cause the secondary injury to the patient.

Third disadvantage: Since the image display panel 20 is connected with the first end 11 of the lens handle 10, when the medical personnel pushes the lens handle 10 forward and upward to press the combined lens blade 60 against the patient's tongue, the angle or direction of the image display panel 20 is also changed. Thus, the medical personnel may not see the image displayed on the image display panel 20 smoothly when performing tracheal intubation, and the angle needs to be adjusted again, which affects the fluency of the tracheal intubation operation. Due to the narrow viewing angle, it will cause a lot of time to iteratively adjust the angle to capture a visible and identifiable image, which is very inconvenient.

Therefore, it is desired to provide a laryngoscope that can overcome the above-mentioned limitations of the conventional direct laryngoscope and video laryngoscope, so that the operator can effectively, quickly and safely complete the extremely challenged and urgent tracheal intubation. Pursuing safety and benefits of patients is a continuous and important goal of emergency and intensive care medicine.

SUMMARY

In view of the foregoing, an objective of the present disclosure is to provide a video laryngoscope, which can overcome the problem of the conventional video laryngoscope with insufficient viewing angle that cannot effectively capture the image of the position of trachea at the patient's larynx, does not need to change the laryngoscope spatula blade of different curvatures, and can avoid time-consuming iterative adjustments to capture visible and identifiable images. That is, it is possible to observe the position of trachea at the patient's larynx with a wider viewing angle through multiple image capturing devices in real time and at the same time, so that the medical personal can quickly perform endotracheal intubation, effectively shorten the intubation time, and complete the extremely challenged and urgent endotracheal intubation steps smoothly. In addition to overcoming the above three limitations of conventional video laryngoscope, this disclosure further configures an imaging device on the front end of the hyperangulated blade for capturing the glottis image that cannot be directly seen in extremely difficult intubation conditions (fourth disadvantage), thereby solving the long-term difficulty in endotracheal intubation. In other words, the spatula blade is designed with a large curvature, so that the multi-view video laryngoscope can be used not only for routine endotracheal intubation, but also for difficult airway. Another potential danger (fifth disadvantage) of conventional direct vision or video laryngoscopy is that when the endotracheal intubation begins to insert the blade into the mouth to explore the glottis, there is a risk of injuring the mouth and throat tissues during the early blind period that the direct vision or image assistance is not available. For this conventional disadvantage, the most advanced image capturing apparatus of this disclosure can monitor the entire endotracheal intubation process from the beginning to avoid this complication. Finally, the sixth disadvantage, the configuration of multiple image capturing apparatuses can have one more chance of survival, avoid being covered by blood and sputum, and complete endotracheal intubation more effectively, quickly and safely.

To achieve the above objective, a multi-view video laryngoscope includes a handle, a spatula blade, a first image capturing apparatus and a second image capturing apparatus. The spatula blade is detachably connected to the handle, and the spatula blade includes a junction, a side plate and a transverse plate. The junction is detachably connected to one end of the handle. The side plate extends outwards from the junction. The transverse plate bends and extends outwards from one side of the side plate. The first image capturing apparatus is arranged on the side of the side plate that is away from the transverse plate, and the first image capturing apparatus captures a first image. The second image capturing apparatus is arranged on the transverse plate and located on or adjacent to a central axis of the transverse plate. Herein, the second image capturing apparatus is farther away from the junction than the first image capturing apparatus, and the second image capturing apparatus captures a second image.

In one embodiment, the multi-view video laryngoscope further includes a third image capturing apparatus arranged on one side of the transverse plate away from the side plate, wherein the third image capturing apparatus is farther away from the junction than the first image capturing apparatus and is closer to the junction than the second image capturing apparatus, and the third image capturing apparatus captures a third image.

In one embodiment, the spatula blade further includes a bottom plate bending and extending outwards from another side of the side plate, the bottom plate and the transverse plate are arranged at two sides of the side plate, respectively, and the bending and extending direction of the bottom plate from the side plate is different from the bending and extending direction of the transverse plate from the side plate.

In one embodiment, the width of the bottom plate is gradually shrunk from a portion of the bottom plate adjacent to the junction to a portion of the bottom plate away from the junction.

In one embodiment, the width of the transverse plate is gradually shrunk from a portion of the transverse plate adjacent to the junction to a portion of the transverse plate away from the junction.

In one embodiment, an internal portion of the handle is configured with a power supply device, and the first image capturing apparatus, the second image capturing apparatus and the third image capturing apparatus are electrically connected to the power supply device.

In one embodiment, the first image capturing apparatus, the second image capturing apparatus and the third image capturing apparatus are communicated with a monitor by a wireless transmission manner, and the monitor displays the first image, the second image and/or the third image.

In one embodiment, each of the first image capturing apparatus, the second image capturing apparatus and the third image capturing apparatus includes a light source and a camera.

In one embodiment, the central axis of the transverse plate does not intersect the axis line of the handle.

In one embodiment, the transverse plate has a curved structure configuration from one end of the transverse plate close to the junction to one end of the transverse plate away from the junction, the transverse plate has a curved angle, and the curved angle is between 120 degrees and 150 degrees.

In one embodiment, a first included angle is defined between the transverse plate and the side plate, a second included angle is defined between the bottom plate and the side plate, and the first included angle and the second included angle are between 75 degrees and 105 degrees.

To achieve the above objective, a spatula blade configured with multiple image capturing apparatuses of this disclosure is provided, wherein the spatula blade is detachably connected to one end of a handle. The spatula blade includes a junction, a side plate, a transverse plate, a first image capturing apparatus, and a second image capturing apparatus. The junction is detachably connected to the one end of the handle, the side plate extends outwards from the junction, and the transverse plate bends and extends outwards from one side of the side plate. The first image capturing apparatus is arranged on the side of the side plate that is away from the transverse plate; and the second image capturing apparatus is arranged on the transverse plate and located on or adjacent to a central axis of the transverse plate. The second image capturing apparatus is farther away from the junction than the first image capturing apparatus.

As mentioned above, the multi-view video laryngoscope of this disclosure can overcome the limitations of the conventional direct laryngoscope and video laryngoscope, so that the operator can effectively, quickly and safely complete the extremely challenged and urgent tracheal intubation.

BRIEF DESCRIPTION OF THE DRAWINGS

The disclosure will become more fully understood from the detailed description and accompanying drawings, which are given for illustration only, and thus are not limitative of the present disclosure, and wherein.

DETAILED DESCRIPTION OF THE DISCLOSURE

Figure 1A:
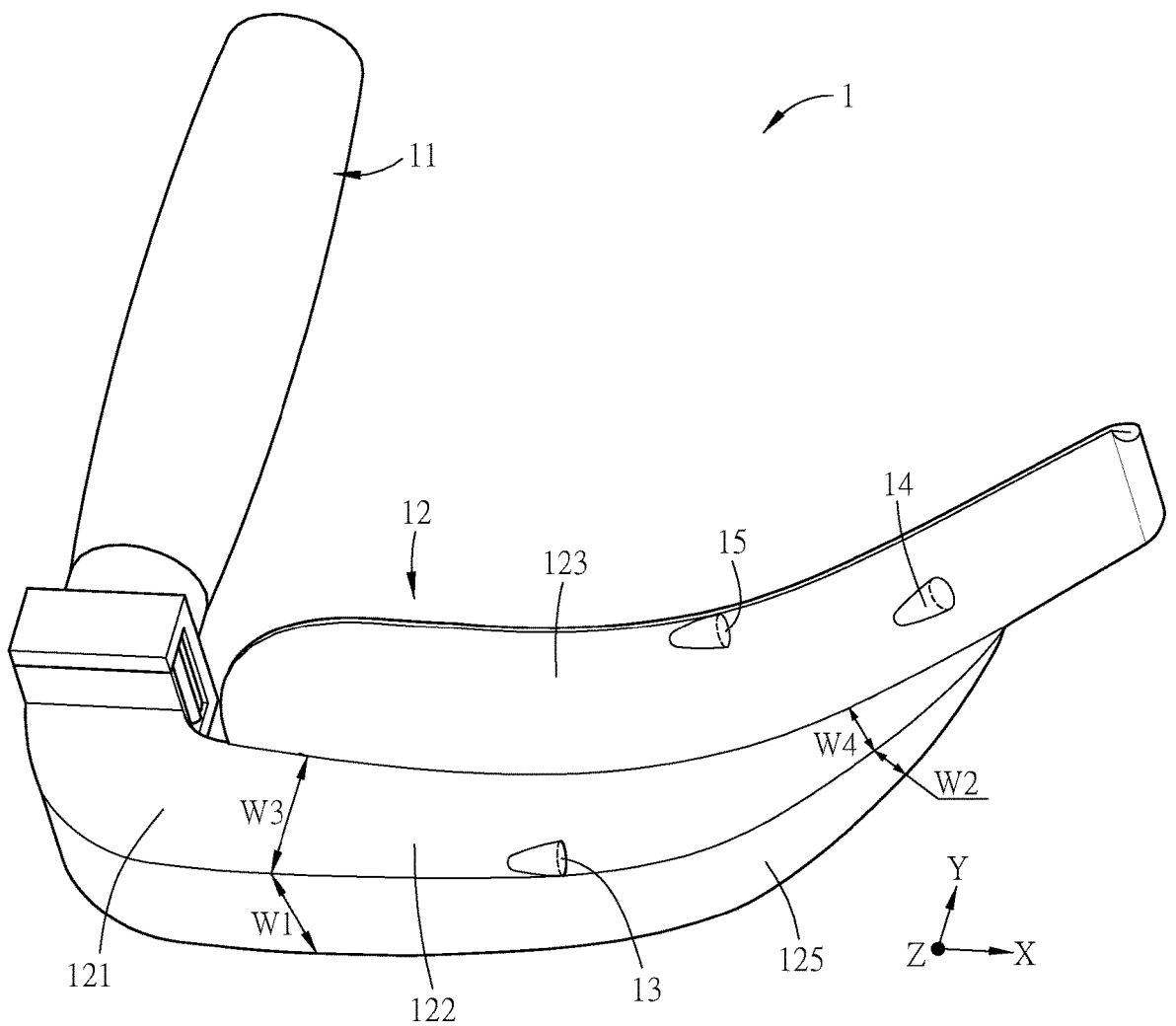
FIG. 1A is a perspective view of a multi-view video laryngoscope according to a first embodiment of this disclosure.

Various embodiments according to the present disclosure will be described below with reference to related drawings, wherein the same components will be described with the same reference numerals.

Figure 1B:
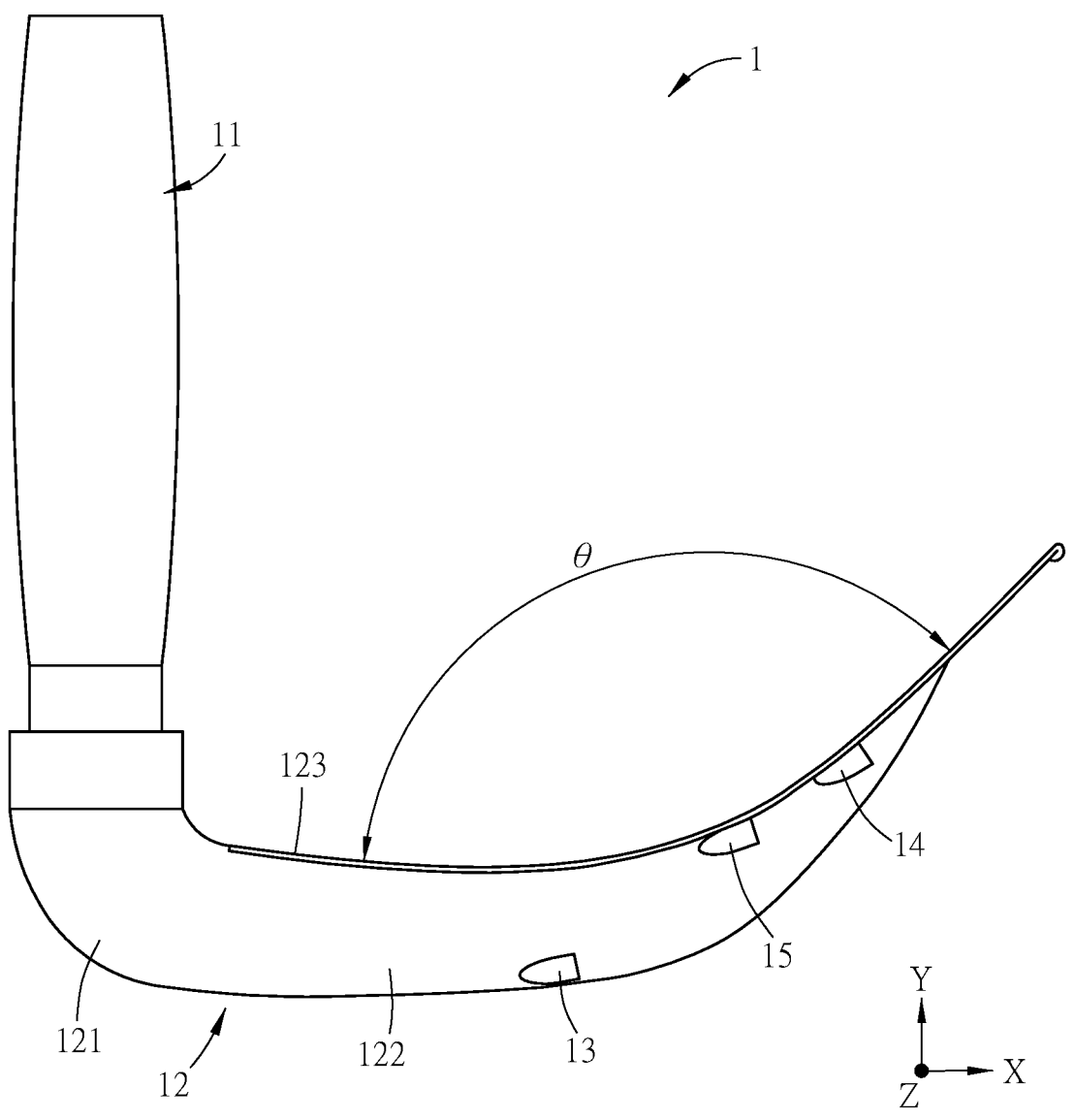
FIG. 1B is another perspective view of the multi-view video laryngoscope of FIG. 1A.
Figure 1C:
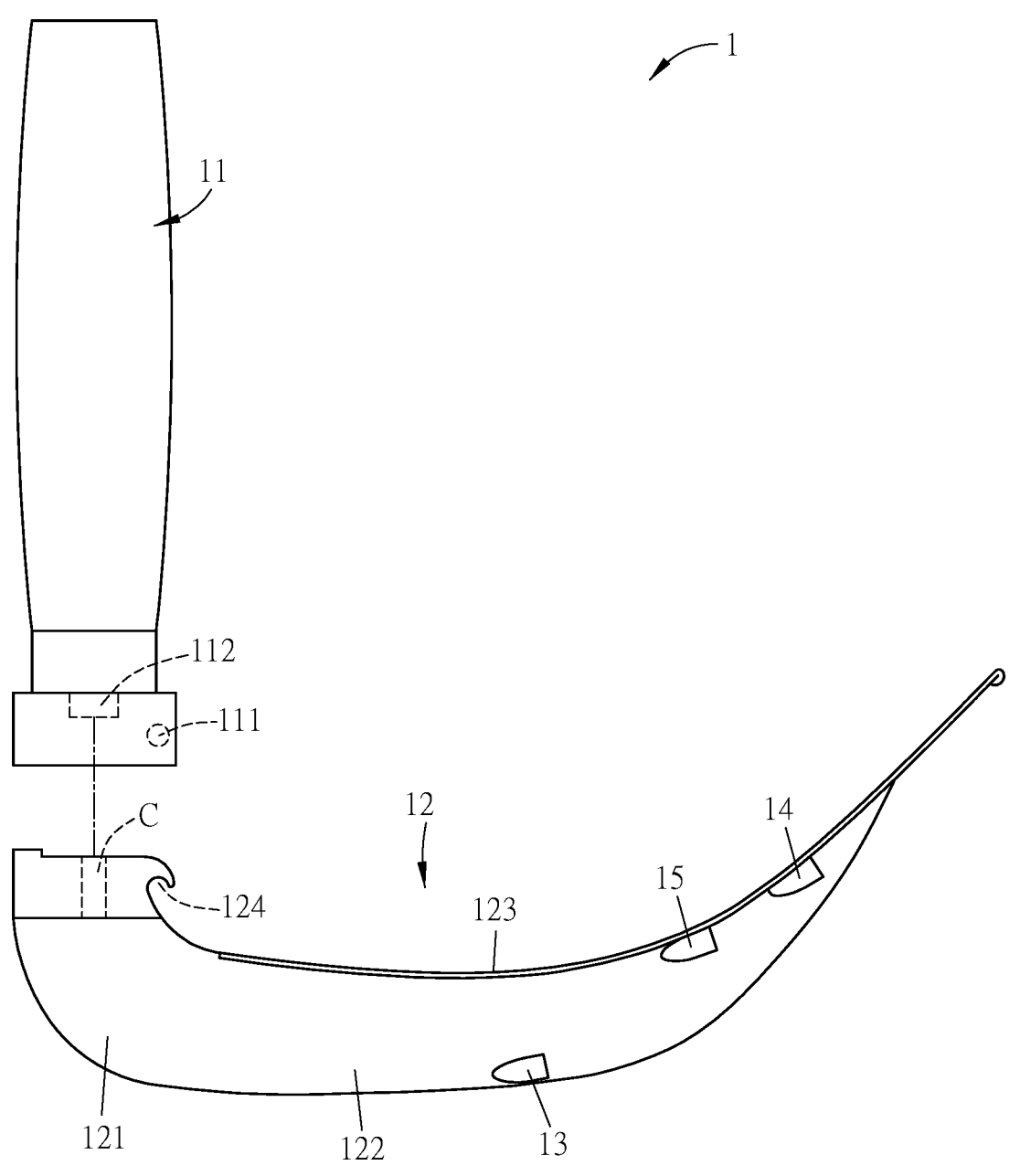
FIG. 1C is an exploded view of the multi-view video laryngoscope of FIG. 1B.
Figure 1D:
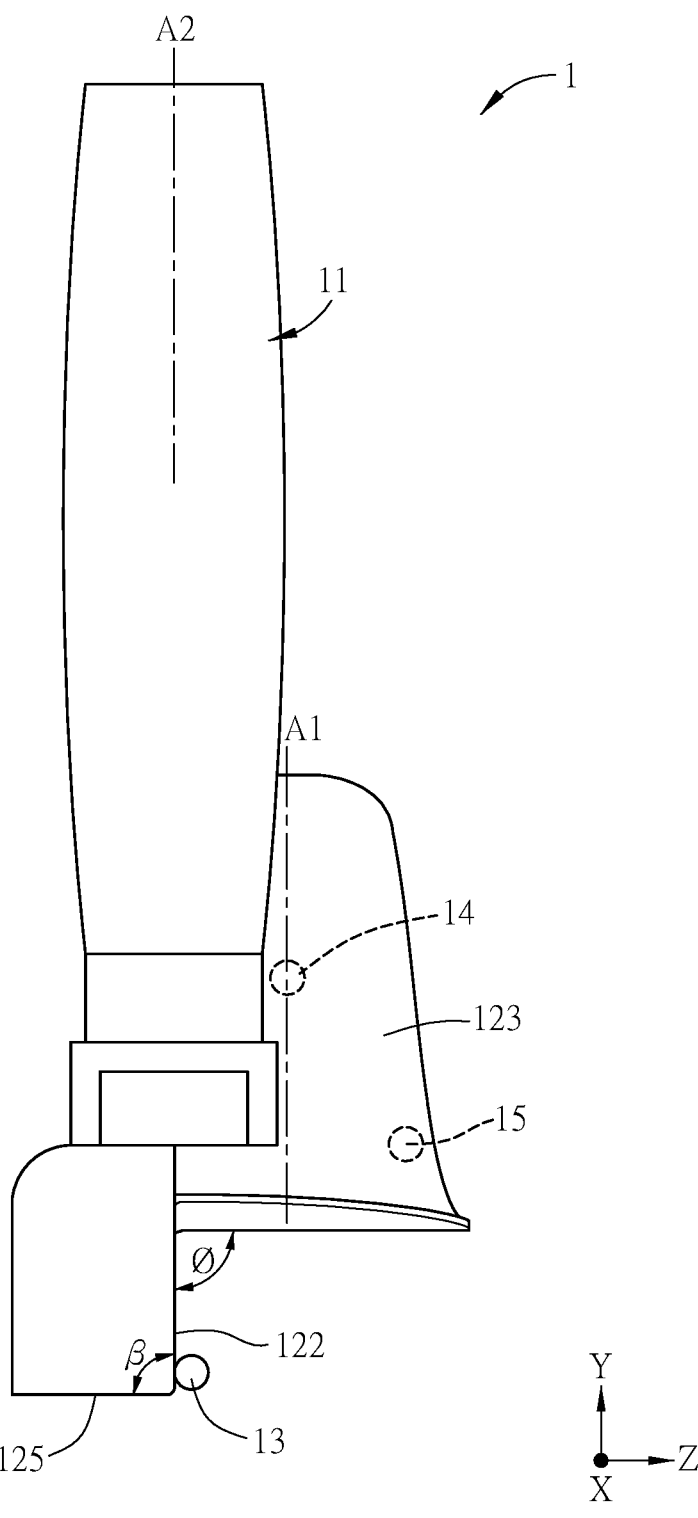
FIG. 1D is another perspective view of the multi-view video laryngoscope of FIG. 1A.
Figure 2:
FIG. 2 is a schematic diagram showing the multi-view video laryngoscope of this disclosure in use.

Please refer to FIG. 1A to FIG. 1D in view of FIG. 2. FIG. 1A is a perspective view of a multi-view video laryngoscope according to a first embodiment of this disclosure. FIG. 1B is another perspective view of the multi-view video laryngoscope of FIG. 1A. FIG. 1C is an exploded view of the multi-view video laryngoscope of FIG. 1B. FIG. 1D is another perspective view of the multi-view video laryngoscope of FIG. 1A. FIG. 2 is a schematic diagram showing the multi-view video laryngoscope of this disclosure in use. In this embodiment, the multi-view video laryngoscope 1 includes a handle 11, a spatula blade 12, a first image capturing apparatus 13, and a second image capturing apparatus 14. The spatula blade 12 is detachably connected to the handle 11. The spatula blade 12 includes a junction 121, a side plate 122, and a transverse plate 123. The junction 121 is detachably connected to one end of the handle 11. The side plate 122 extends outwards from the junction 121. The transverse plate 123 bends and extends outwards from one side of the side plate 122. As shown in FIG. 1A, the side plate 122 extends outwards from the junction 121 roughly in, for example but not limited to, the X-axis direction, and the transverse plate 123 bends and extends outwards from the upper side of the side plate 122 in, for example but not limited to, the Z-axis direction.

The first image capturing apparatus 13 is arranged on the side of the side plate 122 that is away from the transverse plate 123, and the first image capturing apparatus 13 captures a first image P1. The second image capturing apparatus 14 is arranged on the transverse plate 123 and located on or adjacent to a central axis A1 of the transverse plate 123. The second image capturing apparatus 14 is farther away from the junction 121 than the first image capturing apparatus 13, and the second image capturing apparatus 14 captures a second image P2.

As shown in FIGS. 1A and 1B, the handle 11 is arranged along the Y-axis direction, the junction 121 of the spatula blade 12 is detachably connected to one end of the handle 11, and the side plate 122 extends outwards from the junction 121 (approximately extends in the direction away from the junction 121 and the handle 11 (i.e., approximately in the X-axis direction as shown in FIG. 1A and FIG. 1B)). The transverse plate 123 extends outwards from the side plate 122 (in the direction away from the side plate 122 (i.e., in the Z-axis direction as shown in FIG. 1A). In this case, the first included angle θ defined between the transverse plate 123 and the side plate 122 is, for example but not limited to, 45, 60, 75, 90 or 105 degrees. Preferably, the first included angle θ defined between the transverse plate 123 and the side plate 122 is 90 degrees (as shown in FIG. 1D). In particular, as shown in FIG. 1B, the transverse plate 123 has a curved structure configuration from one end thereof close to the junction 121 to another end thereof away from the junction 121. The transverse plate 123 has a curved angle θ, and the curved angle θ is, for example but not limited to, 120, 135 or 150 degrees. Preferably, the curved angle θ is 135 degrees. The spatula blade 12 is designed with a large curve radian, so that the multi-view video laryngoscope 1 can be used not only for routine endotracheal intubation, but also for difficult airway. In addition, for example, but not limited to, as shown in FIGS. 1A to 1D, the first image capturing apparatus 13 is arranged at the bottom of the side plate 122 (i.e., the lowest of the side plate 122), and the second image capturing apparatus 14 is arranged adjacent to one end of the transverse plate 123 farther away from the handle 11. Both of the first image capturing apparatus 13 and the second image capturing apparatus 14 can be used to capture images from different angles to achieve the effect of capturing multi-view images.

As shown in FIG. 1B and FIG. 1C, the handle 11 may include an engaging portion 111, and the spatula blade 12 may include an engaging portion 124. The structures of the engaging portions 111 and 124 are corresponding to each other, so that the spatula blade 12 is detachably connected to the handle 11. In particular, although the engaging portion 111 is a pivot and the engaging portion 124 is a hook as an example, the engaging portion 111 and the engaging portion 124 can also be a pair of protrusion and recess, or any of other engaging structures that are known to those skilled in the art as long as the engaging portion 111 and the engaging portion 124 can be detachably connected to each other. This disclosure is not limited thereto. In addition, during the intubation process, the spatula blade 12 is used to press against the patient's tongue, and the end of the spatula blade 12 away from the junction 121 and the handle 11 (the position adjacent to the second image capturing apparatus 14) is used to lift the position of the epiglottis cartilage.

Referring to FIG. 1A to FIG. 1D again, in this embodiment, the multi-view video laryngoscope 1 can further include a third image capturing apparatus 15, which is disposed on the side of the transverse plate 123 away from the side plate 122, and the third image capturing apparatus 15 is farther away from the junction 121 than the first image capturing apparatus 13 and is closer to the junction 121 than the second image capturing apparatus 14. The third image capturing apparatus 15 captures a third image P3. As shown in FIG. 1A and FIG. 1B, the third image capturing apparatus 15 is farther away from the junction 121 than the first image capturing apparatus 13, and is closer to the junction 121 than the second image capturing apparatus 14. That is, the first image capturing apparatus 13, the third image capturing apparatus 15 and the second image capturing apparatus 14 are arranged in sequence from the place adjacent to the junction 121 to the place far away from the junction 121. The distances between the three image capturing apparatuses 13-15 and the junction 121 are different (refer to the X-axis), and the heights of the three image capturing apparatuses are also different with comparing to the handle 11 (refer to the Y-axis). In addition, as shown in FIG. 1D, the third image capturing apparatus 15 is arranged on the side of the transverse plate 123 away from the side plate 122, and the distances between the three image capturing apparatuses 13-15 and the handle 11 are different in the Z-axis direction. The first image capturing apparatus 13, the second image capturing apparatus 14 and the third image capturing apparatus 15 are arranged in sequence from the place adjacent to the handle 11 to the place far away from the handle 11. Referring to FIGS. 1A to 1D, the three image capturing apparatuses 13-15 of the multi-view video laryngoscope 1 are installed at different positions in the X-axis, Y-axis and Z-axis directions, so they can each provide the first image P1, the second image P2 and the third image P3 from different viewing angles. Herein, the three images P1-P3 may partially overlap each other or not, so that the medical personal can see the position of the glottis more clearly during subsequent intubation. In particular, compared to the transverse plate 123 of the multi-view video laryngoscope 1 that only includes the first image capturing apparatus 13 and the second image capturing apparatus 14, when the multi-view video laryngoscope 1 further includes a third image capturing apparatus 15, the width of the transverse plate 123 can be increased by 50%, so that the distance between the second image capturing apparatus 14 and the third image capturing apparatus 15 in the Z-axis direction is longer (please refer to FIG. 1D), thereby decreasing the chance of mutual interference. In addition, in FIG. 1D, the positions of the first image capturing apparatus 13, the second image capturing apparatus 14, and the third image capturing apparatus 15 are represent by circles, which are only for illustration and are not used to limit the shapes of the first image capturing apparatus 13, the second image capturing apparatus 14, and the third image capturing apparatus 15.

Please refer to FIG. 1A and FIG. 1D again. In this embodiment, the spatula blade 12 may further include a bottom plate 125, which bends and extends outwards from the other side of the side plate 122. For example, but not limited to, as shown in FIG. 1A, the side plate 122 extends outwards from the junction 121 in the X-axis direction, and the bottom plate 125 bends from the lower side of the side plate 122 and extends outwards in the Z-axis direction, so that the bottom plate 125 and the transverse plate 123 are located at two sides of the side plate 122. As shown in FIG. 1A and FIG. 1D, the handle 11 is arranged along the Y-axis direction, and the side plate 122 extends outwards from the junction 121 (in the direction away from the junction 121 and the handle 11 (i.e., the X-axis direction in FIG. 1A)). The transverse plate 123 and the bottom plate 125 respectively extend outwardly from the side plate 122 (in the direction away from the side plate 122 (i.e., the Z-axis direction in FIG. 1D)), so that the transverse plate 123 and the bottom plate 125 are located at two ends and two sides of the side plate 122, and respectively extend from the side plate 122 in different directions (in the Z-axis direction and the –Z-axis direction). The transverse plate 123 is disposed on one end of the side plate 122 adjacent to the handle 11, and the bottom plate 125 is disposed on another end of the side plate 122 away from the handle 11. The configuration of the bottom plate 125 can make the operator to move the patient's tongue more easily with the multi-view video laryngoscope 1 during the subsequent intubation process. In addition, the second included angle R defined between the bottom plate 125 and the side plate 122 is, for example but not limited to, 45, 60, 75, 90 or 105 degrees. Preferably, the second included angle R defined between the bottom plate 125 and the side plate 122 is 90 degrees (as shown in FIG. 1D).

Please refer to FIG. 1A again. In this embodiment, the width of the bottom plate 125 is gradually shrunk from one portion thereof adjacent to the junction 121 to another portion thereof away from the junction 121. Specifically, one end of the bottom plate 125 adjacent to the junction 121 has a width W1, and another end of the bottom plate 125 away from the junction 121 has a width W2. The width W1 is greater than the width W2, and the width W2 can be down to zero at the end of the bottom plate 125 close to the transverse plate 123.

In this embodiment, the width of the side plate 122 is gradually shrunk from one portion thereof adjacent to the junction 121 to another portion thereof away from the junction 121. Specifically, one end of the side plate 122 adjacent to the junction 121 has a width W3, and another end of the side plate 122 away from the joint portion 121 has a width W4. The width W3 is greater than the width W4, and the width W4 can be down to zero at the end of the side plate 122 close to the transverse plate 123. The widths of the bottom plate 125 and the side plate 122 are gradually shrunk from the portions adjacent to the junction 121 to the portion away from the junction 121, so that the multi-view video laryngoscope 1 can be inserted into the patient's mouth more easily during the intubation process, and can make patient feel more comfortable.

Figure 1E:
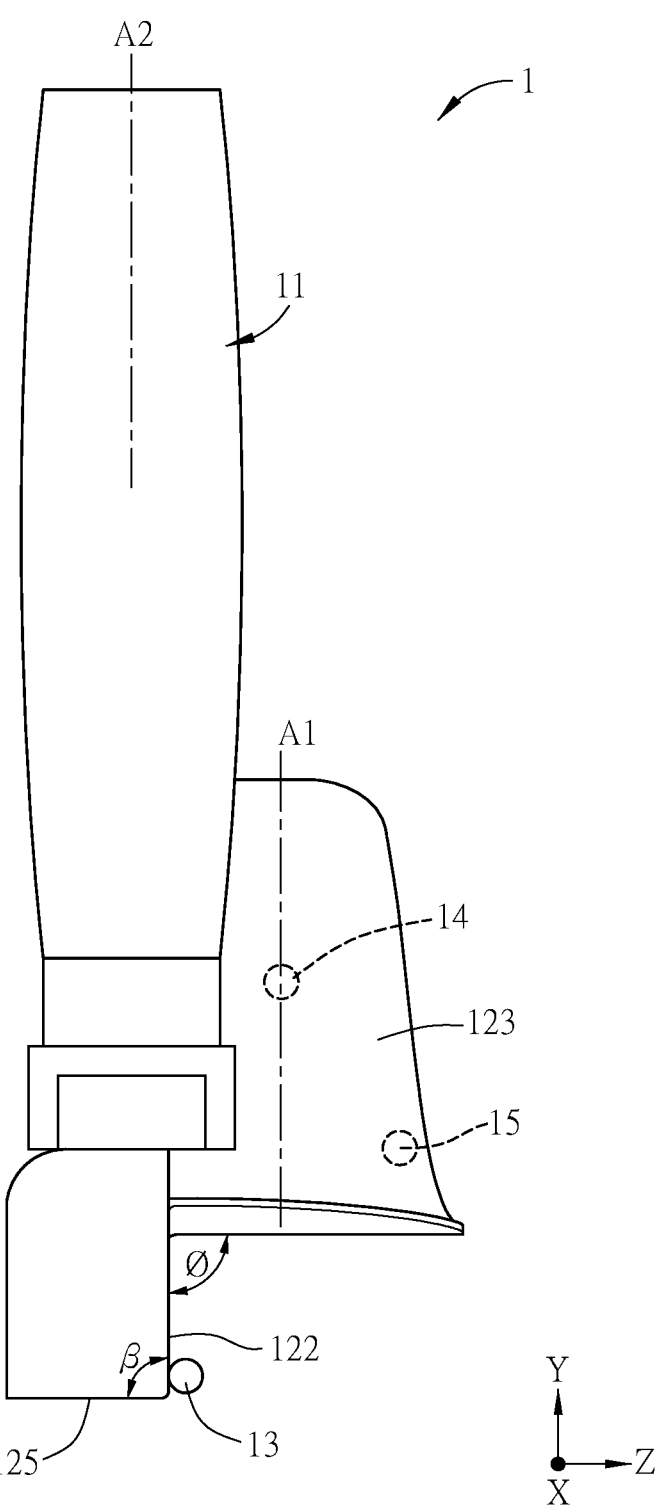
FIG. 1E is schematic diagram showing a transform mode of the multi-view video laryngoscope of FIG. 1D.

Please refer to FIG. 1D again. In this embodiment, the central axis A1 of the transverse plate 123 does not intersect the axis line A2 that passing through the axis of the handle. In other words, the spatula blade 12 is arranged closer to the right side of FIG. 1D than the axis line A2 of the handle. When the patient is lying flat and the medical personal is standing aside the patient's head, it is convenient for the medical personal to put the multi-view video laryngoscope 1 into the patient's mouth from the right side of the patient's mouth, and then move the multi-view video laryngoscope 1 to the middle and left of the patient's mouth to press against the patient's tongue. At this time, the open space between the transverse plate 123 and the side plate 122 (the intubation position of the endotracheal tube) is located in the middle in the mouth, so as to facilitate the operation of endotracheal intubation. In addition, FIG. 1E shows that the relative positions of the side plate 122 and the handle 11 can be changed according to actual needs, so as to facilitate the operation of endotracheal intubation.

Please refer to FIG. 1C. In the multi-view video laryngoscope 1 of the aforementioned embodiment, a power supply device 112 can be configured inside the handle 11, and the first image capturing apparatus 13, the second image capturing apparatus 14 and the third image capturing apparatus 15 can be respectively electrically connected to the power supply device 112. The power supply device 112 can be, for example but not limited to, a disposable battery or a rechargeable battery. The disposable battery can be, for example but not limited to, carbon-zinc battery, alkaline-manganese battery, lithium battery, zinc battery, zinc-mercury battery, mercury battery, magnesium-manganese battery or any of other disposable batteries known to those skilled in the art. The rechargeable battery can be, for example but not limited to, lead-acid battery, nickel-cadmium battery, nickel-metal hydride battery, lithium-ion battery, or any of other rechargeable batteries known to those skilled in the art. Specifically, the first image capturing apparatus 13, the second image capturing apparatus 14, and the third image capturing apparatus 15 can be electrically connected to the power supply device 112 through the contact point C, for turning on or off the first image capturing apparatus 13, the second image capturing apparatus 14, and the third image capturing apparatus 15. For example, the power wires of the first image capturing apparatus 13, the second image capturing apparatus 14 and the third image capturing apparatus 15 can be electrically connected the contact point C along the side plate 122 or the transverse plate 123 (to make the drawings concise and clear, the power wires of the first image capturing apparatus 13, the second image capturing apparatus 14 and the third image capturing apparatus 15 are not shown), and then electrically connected to the power supply device 112 through the contact point C. In particular, when the power supply device 112 is a rechargeable battery, the multi-view video laryngoscope 1 may further include a wireless charging member (not shown), or the multi-view video laryngoscope 1 may further include a wired charging member (not shown) for charging the power supply device 112. When the multi-view video laryngoscope 1 is configured with a wired charging member, the handle 11 will be provided with a corresponding charging hole, which is used to connect with the city power for charging the power supply device 112, thereby extending the operation time of the multi-view video laryngoscope 1.

In the aforementioned embodiment, each of the first image capturing apparatus 13, the second image capturing apparatus 14 and the third image capturing apparatus 15 may include a light source and a camera (not shown). Specifically, each of the first image capturing apparatus 13, the second image capturing apparatus 14, and the third image capturing apparatus 15 integrates a light source and a camera, so that the first image capturing apparatus 13, the second image capturing apparatus 14, and the third image capturing apparatus 15 can each provide the light source and capture images at the same time. Then, the medical personal can not only observe directly from the patient's mouth with the naked eyes based on the light sources provided by the first image capturing apparatus 13, the second image capturing apparatus 14, and the third image capturing apparatus 15, but also observe the images captured by the first image capturing apparatus 13, the second image capturing apparatus 14 and the third image capturing apparatus 15.

Please refer to FIG. 2. In the aforementioned embodiment, the first image capturing apparatus 13, the second image capturing apparatus 14 and the third image capturing apparatus 15 can be connected with the monitor D in a wireless transmission manner, so that the monitor D can display the first image P1, the second image P2 and/or the third image P3. According to actual viewing requirements (for example but not limited to zooming in), the monitor D can display at least one of the three images P1-P3.

The above description is an overview of the structure and shape of the present disclosure, and the effect principle that the present disclosure can achieve and the operation method are stated as follows:

Please refer to FIG. 2 again. When the transverse plate 123 of the spatula blade 12 of the present disclosure presses against the tongue 21 of the patient 2, the position of the epiglottis cartilage 22 can be lifted, and at this moment, the second image capturing apparatus 14 is closer to the patient's trachea 23, while the first image capturing apparatus 13 is farther away from the patient's trachea 23 and closer to the patient's tongue tip 24. Thus, the viewing angles of the first image capturing apparatus 13 and the second image capturing apparatus 14 are different, and the captured first image P1 and the captured second image P2 are partially overlapped. The design of the second image capturing apparatus 14 closer to the patient's trachea 23 allows the operator to observe the position of the spatula blade 12 closest to the patient after the multi-view video laryngoscope 1 is inserted into the patient's mouth, thereby preventing the blind intubation that the medical personal may perform the intubation under the situation of not clearly observing inside the patient's mouth, which may cause the tip of the spatula blade 12 to hurt the patient's mouth or other internal tissues.

In addition, the monitor D of the present disclosure can display two split screens, wherein one split screen can display the first image P1 captured by the first image capturing apparatus 13, and the other split screen can display the second image P2 captured by the second image capturing apparatus 14. Therefore, during the intubation operation, the medical personnel can adjust the angular position of the transverse plate 123 against the patient's tongue 21 in real time with referring to the first image P1 and the second image P2 displayed on the remote monitor D. Therefore, after the first image capturing apparatus 13 or the second image capturing apparatus 14 captures the position of the patient's glottis 25 and trachea 23, the medical personal can smoothly pass the endotracheal tube through the patient's trachea 23 via the transverse plate 123 and the side plate 122 and then insert the endotracheal tube into the patient's glottis 25 while watching the image(s) displayed on the monitor D, thereby completing the intubation process.

In one embodiment, the multi-view video laryngoscope 1 of the present disclosure further includes a third image capturing apparatus 15, which is disposed on the side of the transverse plate 123 away from the side plate 122 and electrically connected to the power supply device inside the handle 11. In this embodiment, the third image capturing apparatus 15 is farther away from the junction 121 than the first image capturing apparatus 13, and is closer to the junction 121 than the second image capturing apparatus 14. The third image capturing apparatus 15 can capture a third image P3, and can transmit the third image P3 to the monitor D by wireless transmission manner. In this case, the monitor D can display three split screens for respectively displaying the first image P1, the second image P2 and the third image P3. Therefore, the overall viewing angle of the present disclosure can be wider, and medical personal can adjust the angular position of the transverse plate 123 pressing against the patient's tongue 21 in real time, so that the first image capturing apparatus 13, the second image capturing apparatus 14 or the third image capturing apparatus 15 can quickly capture the position of the patient's glottis 25 and trachea 23, thereby smoothly performing the intubation operation.

In addition, the spatula blade configured with multiple image capturing apparatuses disclosed in the present disclosure is detachably connected to one end of the handle of the multi-view video laryngoscope, and the spatula blade includes a junction, a side plate, a transverse plate, a first image capturing apparatus, and a second image capturing apparatus. In addition, the spatula blade can further includes a third image capturing apparatus. Since the junction, the side plate, the transverse plate, the first image capturing apparatus, the second image capturing apparatus and the third image capturing apparatus have been described in detail above, the descriptions thereof will be omitted here.

In summary, in the multi-view video laryngoscope 1 of the present disclosure, the spatula blade 12 includes a first image capturing apparatus 13 and a second image capturing apparatus 14, and may further include a third image capturing apparatus 15. This configuration can increase the overall viewing angle when using the spatula blade 12 to press against the patient's tongue 21, so that the medical personal can quickly observe the positions of the glottis 25 and trachea 23 at the patient's larynx during intubation operation even if the mouth structures of different patients are varied. It is not necessary to change the spatula blade 12 with different curvature, so the intubation operation will not be delayed, and the hypoxia of the patient can be avoided. Therefore, this disclosure is suitable for general routine intubation and difficult airway.

In addition, the first image capturing apparatus 13, the second image capturing apparatus 14, and the third image capturing apparatus 15 of the present disclosure can be connected to a remote monitor D in a wireless transmission manner, so that the monitor D can display the first image P1, the second image P2 and the third image P3. Therefore, during the intubation operation, the medical personnel can smoothly observe the positions of the glottis 25 and the trachea 23 at the patient's larynx shown on the monitor D. This is actually very convenient, and can increase the fluency of intubation operation, so that the intubation operation can be completed more quickly. Furthermore, the configuration of the first image capturing apparatus 13, the second image capturing apparatus 14 and the third image capturing apparatus 15 can prevent the image capturing apparatus from being affected by the patient's sputum, blood clot, secretion or vomit at the same time. When one of the image capturing apparatuses is defaced, the positions of the patient's glottis 25 and trachea 23 can still be observed through other image capturing apparatuses, so as to avoid the intubation process being affected.

The above descriptions are illustrative only and are not restrictive. Any equivalent modifications or changes made without departing from the spirit and scope of the present disclosure shall be included in the scope of the appended claims.

What is claimed is:

1. A multi-view video laryngoscope, comprising:
   a handle;
   a spatula blade detachably connected to the handle, wherein the spatula blade comprises:
   a junction detachably connected to one end of the handle,
   a side plate extending outwards from the junction, and
   a transverse plate bending and extending outwards from one side of the side plate;
   a first image capturing apparatus arranged on the side of the side plate that is away from the transverse plate, and capturing a first image; and
   a second image capturing apparatus arranged on the transverse plate and located on or adjacent to a central axis of the transverse plate, wherein the second image capturing apparatus is farther away from the junction than the first image capturing apparatus, and captures a second image; and
   a bottom plate bending and extending outwards from another side of the side plate, the bottom plate and the transverse plate are arranged at two sides of the side plate, respectively, and a bending and extending direction of the bottom plate from the side plate is different from a bending and extending direction of the transverse plate from the side plate.

2. The multi-view video laryngoscope of claim 1, further comprising a third image capturing apparatus arranged on one side of the transverse plate away from the side plate, wherein the third image capturing apparatus is farther away from the junction than the first image capturing apparatus and is closer to the junction than the second image capturing apparatus, and the third image capturing apparatus captures a third image.

3. The multi-view video laryngoscope of claim 2, wherein an internal portion of the handle is configured with a power supply device, and the first image capturing apparatus, the second image capturing apparatus and the third image capturing apparatus are electrically connected to the power supply device.

4. The multi-view video laryngoscope of claim 2, wherein the first image capturing apparatus, the second image capturing apparatus and the third image capturing apparatus are communicated with a monitor by a wireless transmission manner, and the monitor displays the first image, the second image and/or the third image.

5. The multi-view video laryngoscope of claim 2, wherein each of the first image capturing apparatus, the second image capturing apparatus and the third image capturing apparatus comprises a light source and a camera.

6. The multi-view video laryngoscope of claim 1, wherein a width of the bottom plate is gradually shrunk from a portion of the bottom plate adjacent to the junction to a portion of the bottom plate away from the junction.

7. The multi-view video laryngoscope of claim 1, wherein a width of the transverse plate is gradually shrunk from a portion of the transverse plate adjacent to the junction to a portion of the transverse plate away from the junction.

8. The multi-view video laryngoscope of claim 1, wherein the central axis of the transverse plate does not intersect an axis line of the handle.

9. The multi-view video laryngoscope of claim 1, wherein the transverse plate has a curved structure configuration from one end of the transverse plate close to the junction to one end of the transverse plate away from the junction, the transverse plate has a curved angle, and the curved angle is between 120 degrees and 150 degrees.

10. The multi-view video laryngoscope of claim 1, wherein a first included angle is defined between the transverse plate and the side plate, a second included angle is defined between the bottom plate and the side plate, and the first included angle and the second included angle are between 75 degrees and 105 degrees.

11. A spatula blade configured with multiple image capturing apparatuses, wherein the spatula blade is detachably connected to one end of a handle, and the spatula blade comprises:
   a junction detachably connected to the one end of the handle;
   a side plate extending outwards from the junction;
   a transverse plate bending and extending outwards from one side of the side plate;
   a first image capturing apparatus arranged on the side of the side plate that is away from the transverse plate;
   a second image capturing apparatus arranged on the transverse plate and located on or adjacent to a central axis of the transverse plate, wherein the second image capturing apparatus is farther away from the junction than the first image capturing apparatus; and
   a bottom plate bending and extending outwards from another side of the side plate, the bottom plate and the transverse plate are arranged at two sides of the side plate, respectively, and a bending and extending direction of the bottom plate from the side plate is different from a bending and extending direction of the transverse plate from the side plate.

12. The spatula blade of claim 11, further comprises a third image capturing apparatus arranged on one side of the transverse plate away from the side plate, wherein the third image capturing apparatus is farther away from the junction than the first image capturing apparatus and is closer to the junction than the second image capturing apparatus.

13. The spatula blade of claim 11, wherein a width of the transverse plate is gradually shrunk from a portion of the transverse plate adjacent to the junction to a portion of the transverse plate away from the junction.

14. The spatula blade of claim 12, wherein each of the first image capturing apparatus, the second image capturing apparatus and the third image capturing apparatus comprises a light source and a camera.

15. The spatula blade of claim 11, wherein the central axis of the transverse plate does not intersect an axis line of the handle.

* * * * *